US008887586B2

(12) United States Patent
Henderson

(10) Patent No.: US 8,887,586 B2
(45) Date of Patent: Nov. 18, 2014

(54) HEAD SPACE SAMPLING DEVICE AND METHOD FOR DETECTING LEAKS IN SAME

(75) Inventor: Robert C Henderson, Avondale, PA (US)

(73) Assignee: Agilent Technologies, Inc., Santa Clara, CA (US)

( * ) Notice: Subject to any disclaimer, the term of this patent is extended or adjusted under 35 U.S.C. 154(b) by 957 days.

(21) Appl. No.: 12/915,542

(22) Filed: Oct. 29, 2010

(65) Prior Publication Data
US 2012/0103068 A1 May 3, 2012

(51) Int. Cl.
G01N 1/22 (2006.01)
G01M 3/32 (2006.01)

(52) U.S. Cl.
CPC ..... *G01M 3/3254* (2013.01); *G01N 2001/2229* (2013.01)
USPC ..... 73/863.01; 73/31.05; 73/40.7; 73/864.63; 340/605; 436/177; 436/181

(58) Field of Classification Search
CPC .................................................. G01N 1/22
USPC .............. 73/23.2, 29.01, 29.03, 29.05, 31.04, 73/31.05, 40.7, 49.2, 49.3, 52, 86, 4.63, 73/40, 23.41, 23.42, 863.01–863.03, 73/864.21, 864.63; 340/605; 436/177, 181
See application file for complete search history.

(56) References Cited

U.S. PATENT DOCUMENTS

| 4,237,733 | A | 12/1980 | Kolb et al. | 73/864.21 |
|---|---|---|---|---|
| 4,373,549 | A | 2/1983 | Nalepa et al. | 137/487.5 |
| 4,464,940 | A | 8/1984 | Pospisil | 73/864.21 |
| 4,558,603 | A | 12/1985 | Chlosta et al. | 73/864.21 |
| 4,994,096 | A | 2/1991 | Klein et al. | 95/15 |
| 5,108,466 | A * | 4/1992 | Klein et al. | 95/1 |
| 5,431,712 | A * | 7/1995 | Henderson et al. | 95/22 |
| 5,476,000 | A | 12/1995 | Henderson et al. | 73/23.27 |
| 5,542,286 | A * | 8/1996 | Wang et al. | 73/23.22 |
| 7,258,132 | B2 * | 8/2007 | Henderson et al. | 137/487.5 |
| 7,709,267 | B2 * | 5/2010 | Tipler et al. | 436/178 |
| 2007/0184553 | A1 * | 8/2007 | Hartlein et al. | 436/50 |
| 2007/0295057 | A1 * | 12/2007 | Tipler et al. | 73/23.39 |

FOREIGN PATENT DOCUMENTS

GB 1179459 A 1/1970

OTHER PUBLICATIONS

TurboMatrix Headspace Sampler and HS 40/110 Trap User's Guide, PerkinElmer, Inc., pp. 1-9, 95-160, 261-269 (2008).

* cited by examiner

*Primary Examiner* — Hezron E Williams
*Assistant Examiner* — Hoang Nguyen

(57) ABSTRACT

The present invention relates to methods and systems for detecting leaks in a head space sampling device. One exemplary method for detecting leaks in a head space sampling device includes establishing fluid communication between a head space and a pressurization gas conduit. Gas pressure and flow rate are monitored within the pressurization gas conduit during pressurization of the head space. Changes in monitored gas pressure and flow rate are used to evaluate whether a leak exists within the head space sampling device or the vial containing the head space. One exemplary head space sampling device includes a conduit for receiving a pressurization gas, flow and pressure sensors for measuring gas flow and pressure within the conduit, a ventilation valve, a pressure valve for controlling gas flow through the conduit, and a controller for processing and controlling pressure and flow through the conduit.

6 Claims, 7 Drawing Sheets

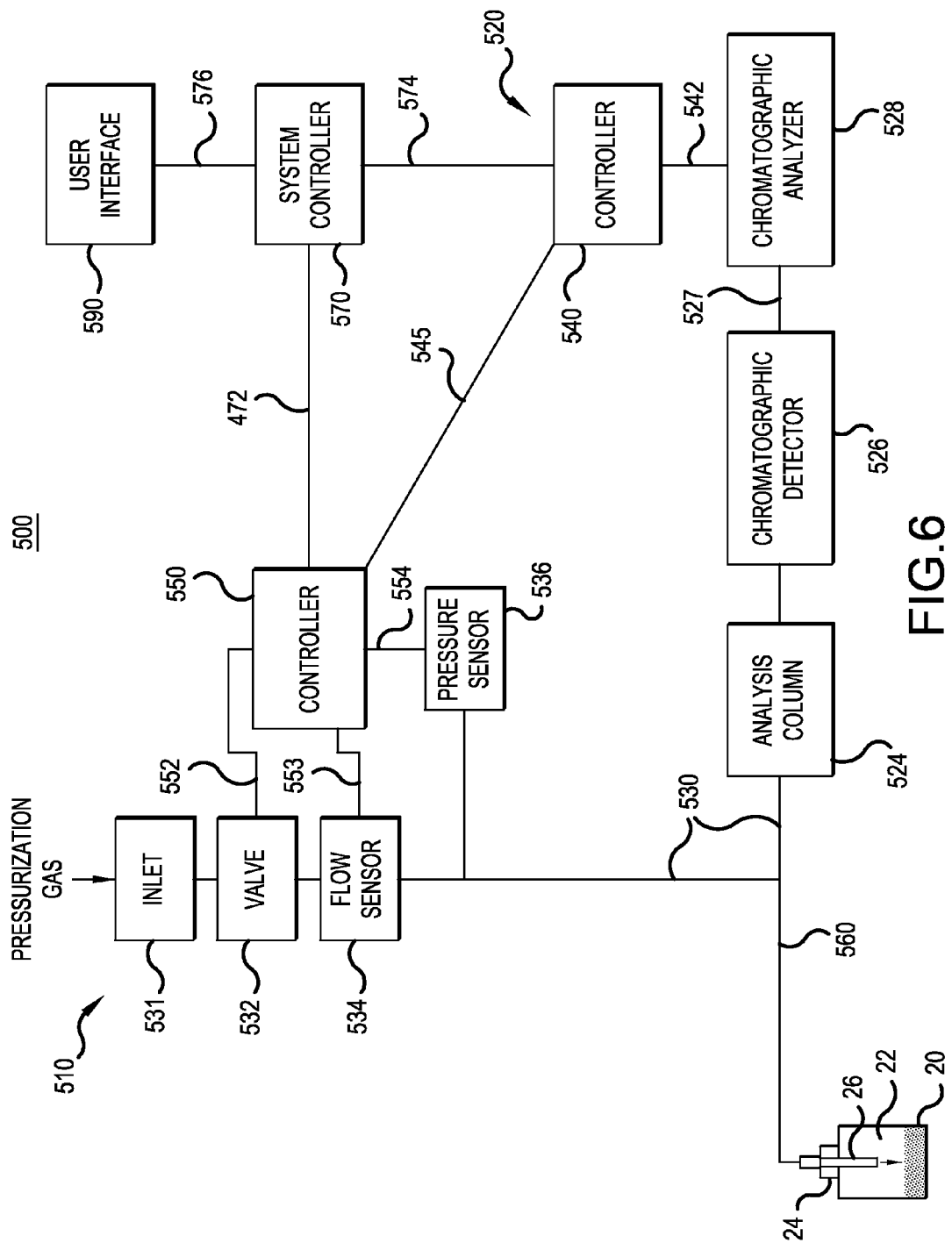

HEAD SPACE SAMPLING DEVICE AND METHOD FOR DETECTING LEAKS IN SAME

FIELD

This invention relates to systems and methods for detecting leaks in a head space sampling device. More particularly, this invention relates to systems and methods for detecting leaks in a head space sampling device by monitoring gas pressure and flow within the head space sampling device.

BACKGROUND

In conventional head space sample analysis, a liquid or solid sample is contained in a vial that is connected to a head space sampling device. The head space sampling device is used to sample the head space above the sample within the vial. Often, the sample is heated to produce a vapor that fills the head space. Prior to sampling of the head space, the vial is often pressurized with a gas that is provided to the vial in a controlled manner. For example, the vial typically can be pressurized by a gas until a selected pressure is reached. When desired pressure characteristics are present within the head space sampling device, the gas from the head space can be directed toward a head space analyzer. Thus, the success of conventional head space analysis systems relies on precisely controlled gas pressures and/or gas flow rates, which help to direct the sampling process. In particular, the presence of leaks within these head space analysis systems can significantly reduce the accuracy and value of any results produced by the systems.

Despite the need for precise control and monitoring of gas pressure and flow rate within conventional head space analysis systems, the leak tests within these systems typically have limited effectiveness. In general, most conventional leak tests either cannot function in an automated manner or are only capable of detecting leaks under particular conditions. For example, many conventional leak tests require specific pressure or temperature conditions or are limited to analysis of specific types of samples. Additionally, many conventional leak tests are only run as part of preventative maintenance procedures rather than as an integral part of individual sample analysis. Furthermore, conventional leak tests generally are only capable of detecting large leaks, thereby allowing more minor leaks to continue throughout sample analysis. Although some dynamic leak test mechanisms do exist, these leak testing mechanisms require specific calibration for each different sample type, each different sample size, and each set of particular pressurization conditions. Most conventional leak tests also are not capable of detecting leaks within the vial containing the sample.

Accordingly, there is a need in the pertinent art for automated and programmable methods for simultaneously detecting leaks of all sizes within a head space analysis system and within a vial containing a sample prior to analysis of the sample. There is a further need in the pertinent art for automated and programmable methods of detecting leaks within a head space analysis system under a variety of pressure conditions and without requiring specific calibration for each sample to be analyzed.

DETAILED DESCRIPTION OF THE FIGURES

These and other features of the preferred embodiments of the invention will become more apparent in the detailed description in which reference is made to the appended drawings wherein.

Figure 5A:
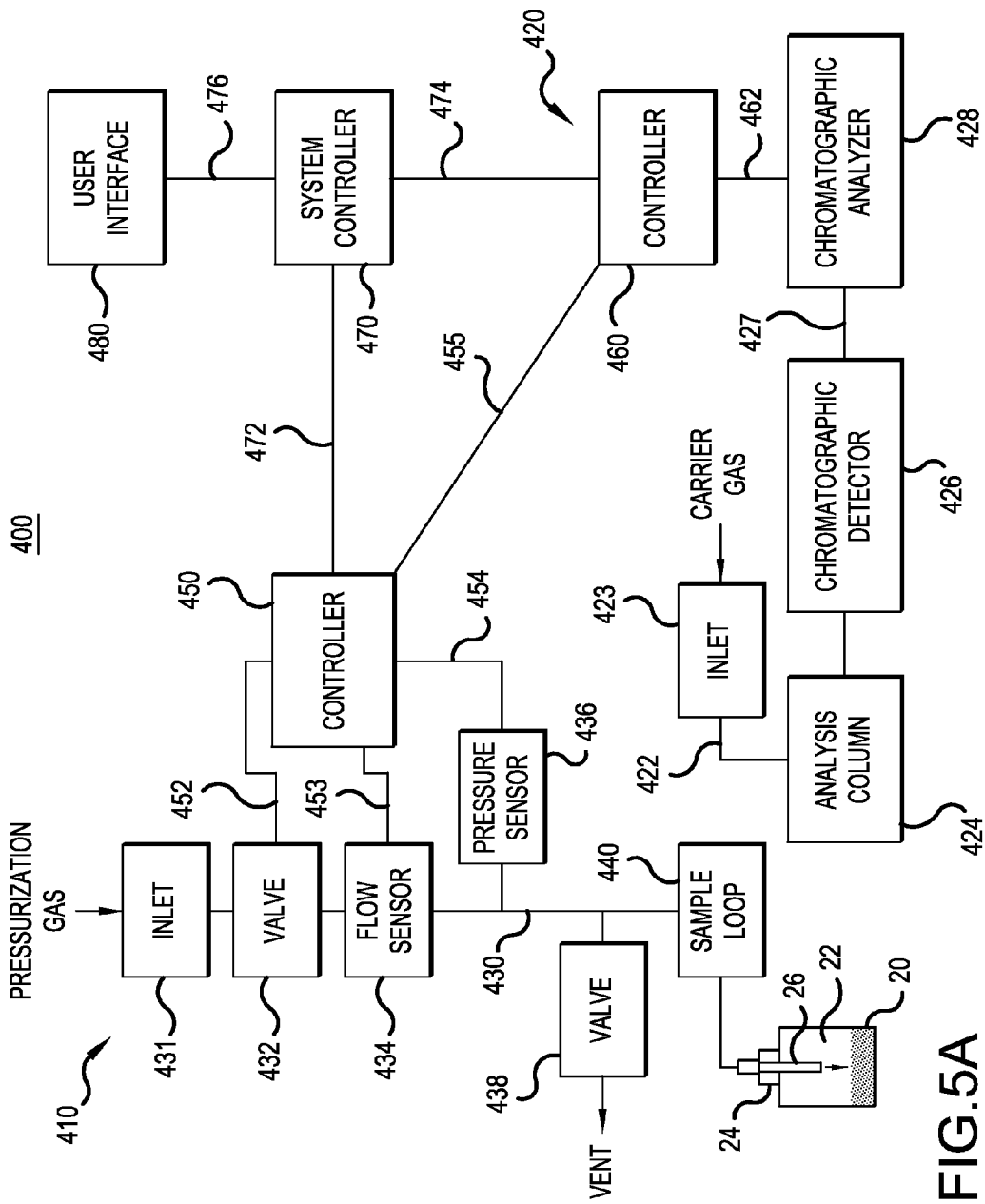
Figure 5B:
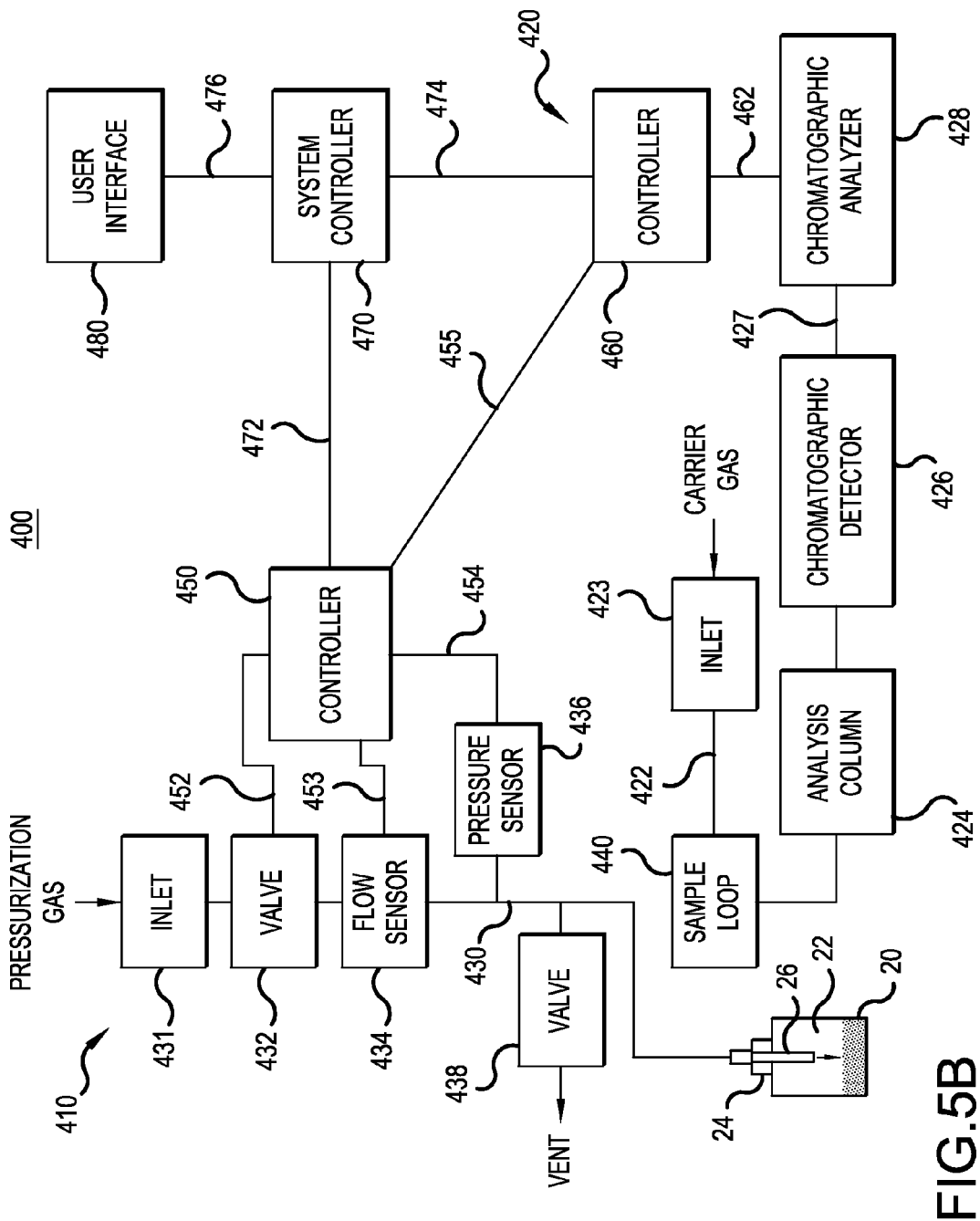

FIGS. 5A and 5B are schematic diagrams of an exemplary head space analysis system, as described herein. FIG. 5A depicts the configuration of the head space analysis system when the sample loop of the system is in fluid communication with the pressurization gas conduit and the vial containing the sample, as described herein. FIG. 5B depicts the configuration of the head space analysis system when the sample loop of the system is in fluid communication with the carrier gas conduit and the analysis column, as described herein.

FIG. 6 depicts a schematic diagram of an exemplary head space analysis system, as described herein. More particularly, FIG. 6 depicts a head space analysis system that is configured to sample a gas sample from the head space of the vial using only a pressurization gas, as described herein.

DETAILED DESCRIPTION

According to various embodiments, methods for detecting leaks in a head space sampling device are disclosed. In some aspects, the head space sampling device can comprise a pressurization gas conduit having an inlet for receiving a pressurization gas, a vial having a head space, and means for establishing fluid communication between the pressurization gas conduit and the vial. In exemplary aspects, the head space sampling device can be configured to sample the head space within the vial.

In one aspect, the methods for detecting leaks in the head space sampling device can comprise pressurizing the pressurization gas conduit with the pressurization gas. In another aspect, the methods for detecting leaks in the head space sampling device can comprise monitoring the gas pressure within the pressurization gas conduit. In an additional aspect, the methods for detecting leaks in the head space sampling device can comprise monitoring the flow rate of the pressurization gas within the pressurization gas conduit. In a further aspect, the methods for detecting leaks in the head space sampling device can comprise establishing fluid communication between the head space and the pressurization gas conduit. In still a further aspect, the methods for detecting leaks in the head space sampling device can comprise determining whether there is a leak based on at least one of the gas pressure within the pressurization gas conduit and the flow rate of the pressurization gas through the pressurization gas conduit.

According to various embodiments, head space sampling devices are also disclosed. In some aspects, the head space sampling devices can be configured to sample a gas sample from a head space of a vial using a pressurization gas.

In one aspect, the head space sampling devices can comprise a pressurization gas conduit in fluid communication with the vial. In this aspect, the pressurization gas conduit can have an inlet for receiving the pressurization gas and a valve for controlling flow of gas therethrough the pressurization gas conduit. In another aspect, the head space sampling device can comprise a flow sensor for measuring gas flow through the pressurization gas conduit. In this aspect, the flow sensor of the head space sampling device can be configured to generate a flow signal indicative of the gas flow through the pressurization gas conduit. In an additional aspect, the head space sampling device can comprise a pressure sensor for measuring gas pressure within the pressurization gas conduit. In this aspect, the pressure sensor of the head space sampling device can be configured to generate a pressure signal indicative of the gas pressure within the pressurization gas conduit. In a further aspect, the head space sampling device can comprise a controller adapted to receive the flow signal from the flow sensor and the pressure signal from the pressure sensor. In this aspect, the controller can be in communication with and control the valve of the pressurization gas conduit by opening and closing the valve to alternately control the flow of the pressurization gas through the pressurization gas conduit and the pressure within the pressurization gas conduit.

According to various embodiments, head space analysis systems, which comprise a head space sampling device and a head space analyzer, are disclosed. In exemplary aspects, the head space analysis systems can sample and analyze a gas sample from a head space of a vial. A head space analyzer is configured to receive a fluid sample from the head space sampling device, send the fluid sample into an analysis apparatus for analysis, and detect and report the result of the analysis. The analysis apparatus can be a user-selectable component that is not supplied with the head space analyzer, for example, a gas chromatography column. Typically, a user chooses a column and fits it into the head space analyzer before operation of the analysis system. After the sample is analyzed by the gas chromatography column, the components of the sample pass through a detector in the head space analyzer for detection. In some embodiments, the head space analyzer may comprise a mass spectrometer. The sample can be directly analyzed and detected by a mass spectrometer without a separation step prior to mass spectrometry. Alternatively, the sample can be analyzed by a chromatography column first, followed by further analysis and detection by a mass spectrometer.

The present invention can be understood more readily by reference to the following detailed description, examples, drawings, and claims, and their previous and following description. However, before the present devices, systems, and/or methods are disclosed and described, it is to be understood that this invention is not limited to the specific devices, systems, and/or methods disclosed unless otherwise specified, as such can, of course, vary. It is also to be understood that the terminology used herein is for the purpose of describing particular aspects only and is not intended to be limiting.

The following description of the invention is provided as an enabling teaching of the invention in its best, currently known embodiment. To this end, those skilled in the relevant art will recognize and appreciate that many changes can be made to the various aspects of the invention described herein, while still obtaining the beneficial results of the present invention. It will also be apparent that some of the desired benefits of the present invention can be obtained by selecting some of the features of the present invention without utilizing other features. Accordingly, those who work in the art will recognize that many modifications and adaptations to the present invention are possible and can even be desirable in certain circumstances and are a part of the present invention. Thus, the following description is provided as illustrative of the principles of the present invention and not in limitation thereof.

In this specification and in the claims that follow, reference will be made to a number of terms that shall be defined to have the following meanings:

As used throughout, the singular forms "a," "an" and "the" include plural referents unless the context clearly dictates otherwise. Thus, for example, reference to "a pressure sensor" can include two or more such pressure sensors unless the context indicates otherwise.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

As used herein, the terms "optional" or "optionally" mean that the subsequently described event or circumstance may or may not occur, and that the description includes instances where said event or circumstance occurs and instances where it does not.

As used herein, the term "head space" refers to the portion of a vial or other container that is filled by gas. Thus, if a solid sample is positioned within the container, the head space will include the portion of the container that is filled by gaseous matter but will not include the portion of the container occupied by the solid sample. Similarly, if only gaseous matter is contained within the container, then the head space will include the entire contents of the container.

As used herein, the term "sample loop" refers to a container for a gas, liquid, or fluid sample. As described herein, a sample loop can be selectively placed in fluid communication with either of a head space sampling device and a head space analyzer. A sample loop is configured to receive at least a portion of a sample from a vial or other sample container in fluid communication with the head space sampling device. After receiving a portion of the sample from the sample container, the sample loop is configured to permit transfer of the sample to the head space analyzer. In some embodiments, the sample loop is configured to allow fluid communication between either the sample loop and the head space analyzer, or the sample loop and a ventilation pathway, but not both. Thus, in these embodiments, when the ventilation pathway is connectable in fluid communication with the pressurization gas conduit, then the sample loop can be configured to allow fluid communication between either the sample loop and the head space analyzer, or the sample loop and the pressurization gas conduit, but not both. As used herein, a sample loop can be, for example and without limitation, a conventional sample loop, a conventional sample trap, a conventional sample cell, and the like, such as the exemplary sample loops described herein.

As used herein, the term "vial" refers to any conventional container that is configured to receive and contain a head space, with or without a gas, liquid, fluid, or solid sample. For example, and without limitation, the vial can be a conventional glass sample vial. It is contemplated that the vial can be configured to contain a head space and sample having a combined volume ranging from about 5 milliliters (mL) to about 22 milliliters (mL). However, any suitable volume for a particular head space and sample can be used as disclosed herein.

Figure 1:
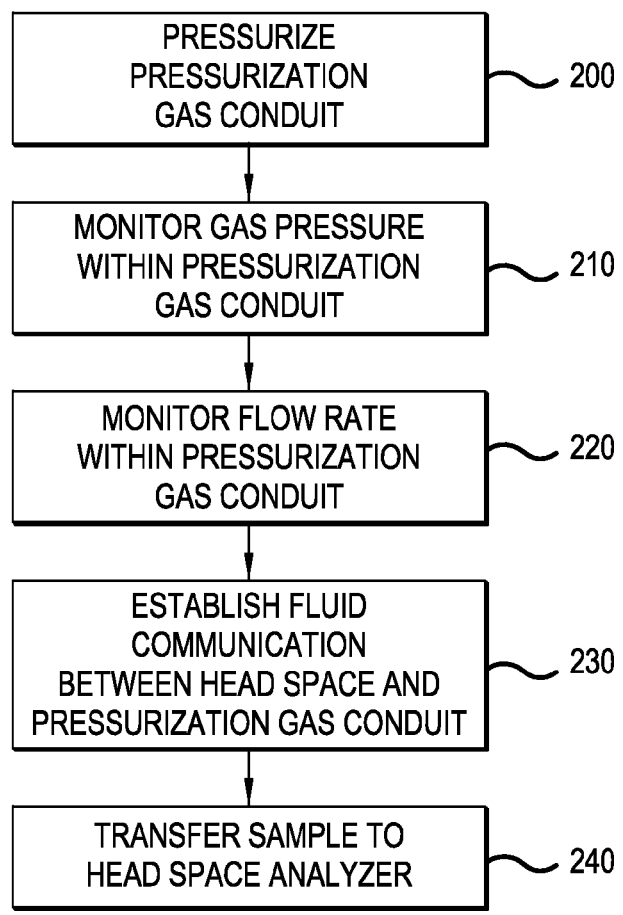
FIG. 1 is a flow chart depicting an exemplary method for detecting leaks in a head space sampling device, as described herein.
Figure 2:
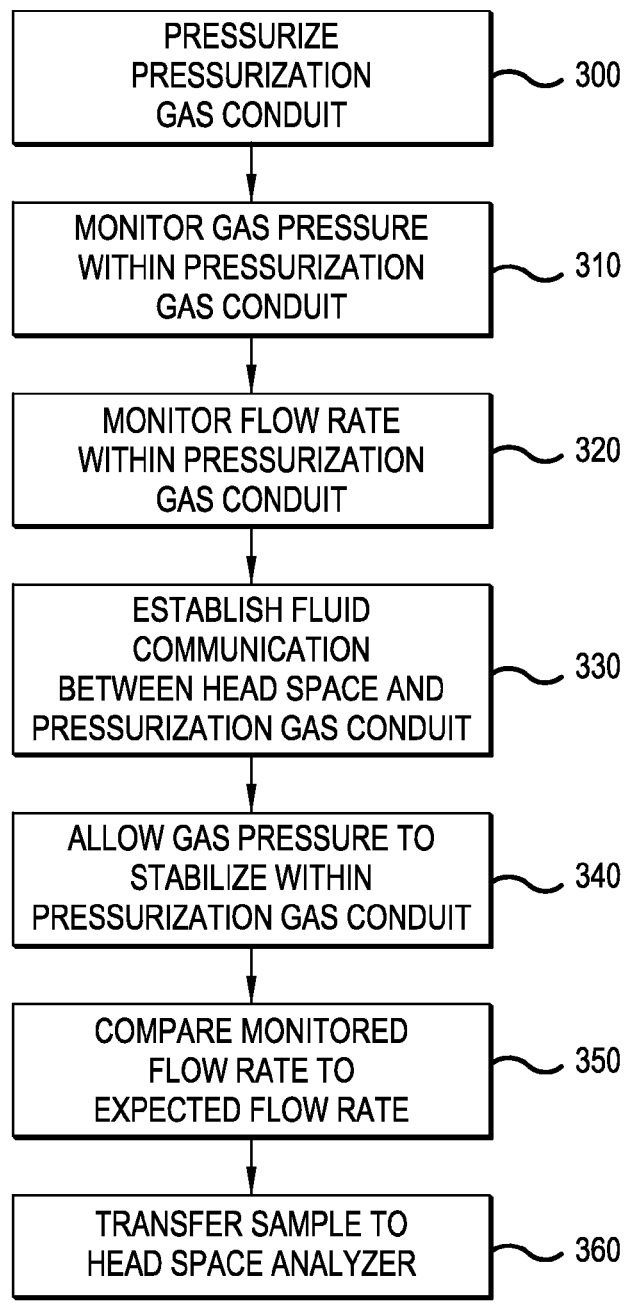
FIG. 2 is a flow chart depicting another exemplary method for detecting leaks in a head space sampling device, as described herein.

Disclosed herein, and as shown in FIGS. 1-2, are methods for detecting leaks in a head space sampling device. In some aspects, the head space sampling device can comprise a pressurization gas conduit having an inlet for receiving a pressurization gas, a vial having a head space, and means for establishing fluid communication between the pressurization gas conduit and the vial. In these aspects, the head space sampling device can be configured to sample the head space within the vial. It is still further contemplated that the pressurization gas can be any gas that is substantially non-reactive or inert for purposes of a particular sample. Thus, it is contemplated that the pressurization gas can be, for example and without limitation, helium gas, hydrogen gas, nitrogen gas, argon gas, and the like. In one exemplary aspect, it is contemplated that the pressurization gas can be a mixture of methane and argon, such as, for example and without limitation, 5% methane in argon.

Figure 3:
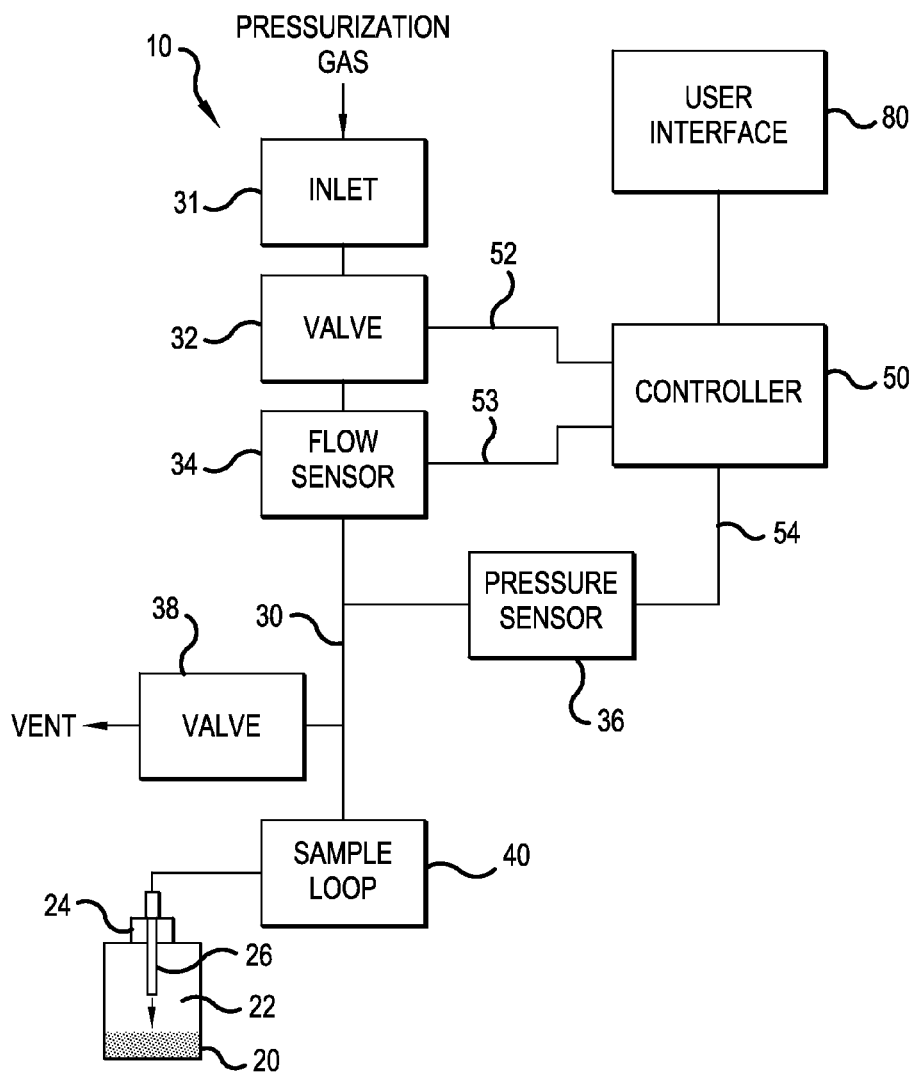
FIG. 3 is a schematic diagram of an exemplary head space sampling device, as described herein.
Figure 4:
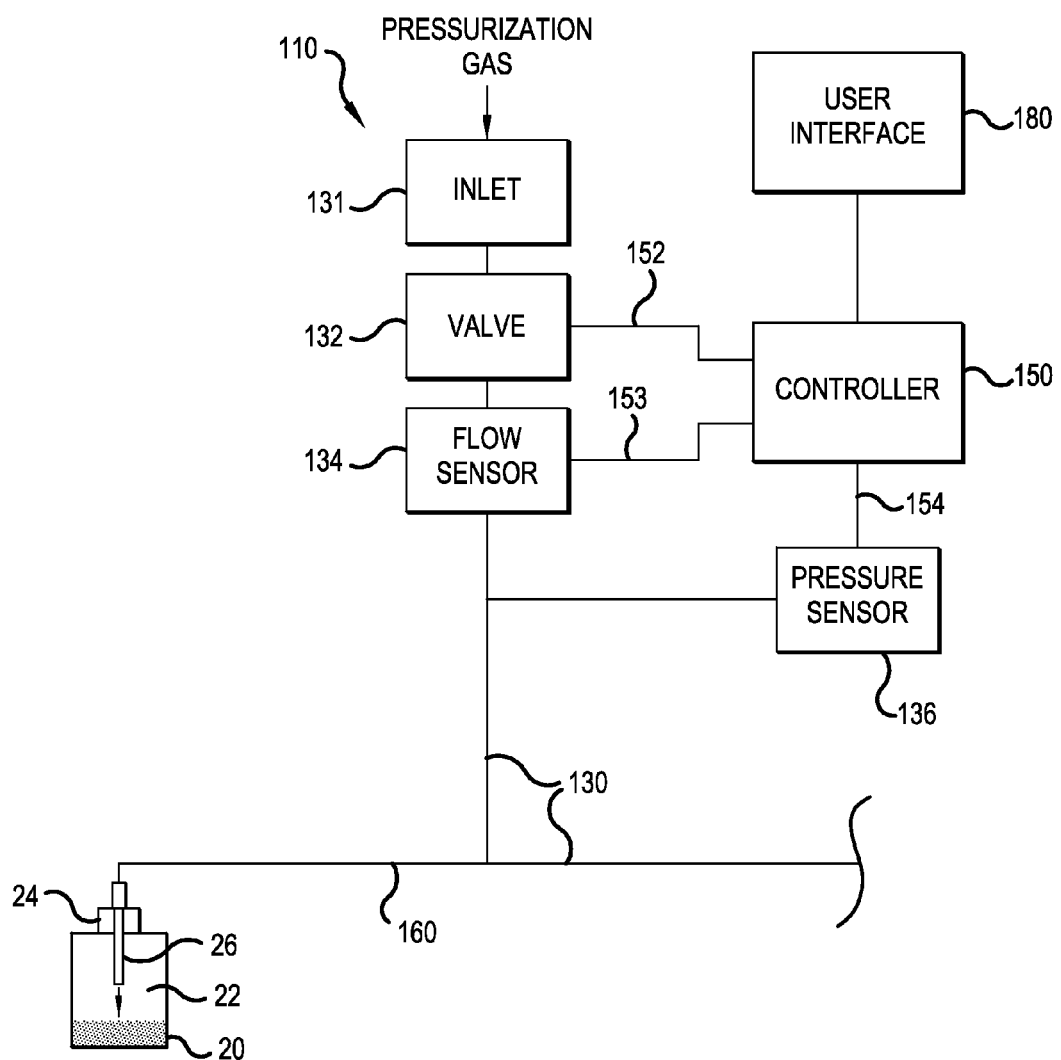
FIG. 4 is a schematic diagram of another exemplary head space sampling device, as described herein.

In exemplary aspects, it is contemplated that the head space sampling device can be a head space sampling device as disclosed herein, such as the head space sampling devices disclosed in FIGS. 3-4 and their corresponding descriptions. It is further contemplated that the head space sampling device can be part of a head space analysis system as disclosed herein, such as the head space analysis systems disclosed in FIGS. 5A, 5B, and 6 and their corresponding descriptions. However, it is contemplated that the disclosed methods can be used to detect leaks in any conventional device for sampling a head space sample, including conventional devices for sampling and analyzing head space samples, such as, for example and without limitation, a gas chromatograph, a mass spectrometer, a gas phase infrared spectrometer, a sensor array, a high performance liquid chromatograph, a liquid spectrometer, and the like.

As shown in FIG. 1, in one aspect, the method for detecting leaks can comprise the step 200 of pressurizing the pressurization gas conduit with a pressurization gas. In another aspect, the method for detecting leaks can comprise the step 210 of monitoring the gas pressure within the pressurization gas conduit. In this aspect, the step 210 of monitoring the gas pressure within the pressurization gas conduit can be accomplished using a conventional pressure sensor positioned in fluid communication with the pressurization gas conduit.

In an additional aspect, as depicted in FIG. 1, the method for detecting leaks can comprise the step 220 of monitoring the flow rate of the pressurization gas through the pressurization gas conduit. In this aspect, the step 220 of monitoring the flow rate of the pressurization gas can be accomplished using a conventional flow sensor positioned in fluid communication with the pressurization gas conduit.

In a further aspect, and with reference to FIG. 1, the method for detecting leaks can comprise the step 230 of establishing fluid communication between the head space and the pressurization gas conduit of the head space sampling device. In this aspect, it is contemplated that the step 230 of establishing fluid communication between the head space and the pressurization gas conduit can comprise penetrating a septum of the vial with a needle having a bore in fluid communication with the pressurization gas conduit, as described herein. It is further contemplated that at least one of the gas pressure with the pressurization gas conduit and the flow rate of the pressurization gas through the pressurization gas conduit can be indicative of whether a leak is present in the head space sampling device. Thus, the method for detecting leaks can further comprise the step of determining whether there is a leak in the head space sampling device based on at least one of the gas pressure within the pressurization gas conduit and the flow rate of the pressurization gas.

Optionally, in an additional aspect, the method for detecting leaks can comprise the step of adjusting the temperature of the vial to produce a vapor in the head space. In this aspect, when the vial contains a sample, it is contemplated that the sample can be heated to produce the vapor in the head space. It is further contemplated that the head space can comprise a gaseous portion of the sample.

Optionally, in a further aspect, prior to the step 230 of establishing fluid communication between the head space and the pressurization gas conduit, the method for detecting leaks can comprise the step of purging the head space sampling device by pressurizing the pressurization gas conduit with the pressurization gas. In this aspect, when the head space sampling device comprises a ventilation valve in fluid communication with the pressurization gas conduit, the ventilation valve can be opened during purging of the head space sampling device.

Optionally, in various aspects, the means for establishing fluid communication between the pressurization gas conduit and the vial can comprise a sample loop as described herein. In these aspects, when the pressurization gas conduit comprises a flow control valve, it is contemplated that in the absence of leaks, at any given time, the measured pressure at any position downstream of the flow control valve within the pressurization gas conduit can be substantially equal to the gas pressure at any other position downstream of the flow control valve within the pressurization gas conduit. Therefore, it is contemplated that the gas pressure within the pressurization gas conduit can be monitored at any position downstream of the flow control valve within the pressurization gas conduit.

In one exemplary aspect, it is contemplated that the sample loop can be attached to, or positioned within, a conventional valve for providing selective fluid communication between the sample loop and elements of the head space sampling device. For example, and without limitation, the sample loop can be attached to, or positioned within, a multi-port valve such as a six-port rotary valve, a multi-port diaphragm valve, and the like. It is further contemplated that the sample loop can be a part of a micro-machined electromechanical system comprising a plurality of multi-port valves or diaphragm valves. It is still further contemplated that the sample loop can be a conventional chemical trap, such as those described herein.

In a further aspect, and with reference to FIG. 1, the step 200 of pressurizing the pressurization gas conduit can comprise pressurizing the pressurization gas conduit to a first pressure. It is contemplated that the pressurization gas conduit can be pressurized to the first pressure after fluid communication has been established between the head space and the pressurization gas conduit. In this aspect, the first pressure can range from about 1 to about 100 pounds per square inch (psi) above ambient pressure, and more preferably from about 5 to about 30 psi above ambient pressure. Alternatively, the first pressure can be referenced to a subambient pressure or to a pressure above ambient pressure. In an additional aspect, the first pressure can be an absolute pressure. In this aspect, the first pressure can range from about 110 to about 800 kiloPascals (kPa), and more preferably from about 130 to about 310 kPa.

In another aspect, the pressurization gas conduit can be pressurized with the pressurization gas at a flow rate ranging from about 5 to about 200 milliliters per minute (mL/min.) referenced to a pressure of 101.3 kPa and a temperature of 25 degrees Celsius. It is contemplated that, in the absence of leaks within the head space sampling device, after the first pressure is achieved, pressure within the pressurization gas conduit should be substantially static, and the flow of gas through the pressurization gas conduit should be substantially zero. Thus, following the establishment of fluid communication between the head space and the pressurization gas conduit, a non-zero flow rate after the first pressure is achieved can be indicative of a leak, such as a leak in one of the vial, the means for establishing fluid communication between the pressurization gas conduit and the vial, and the pressurization gas conduit. It is contemplated that, when leaks are present within the head space sampling device, the pressure within the head space sampling device can be actively maintained by providing additional gas flow within the pressurization gas conduit to compensate for the gas escaping through the leaks. It is further contemplated that, following the establishment of fluid communication between the head space and the pressurization gas conduit, when the supply of pressurization gas is discontinued after the first pressure is achieved, a decreasing pressure can be indicative of a leak, such as a leak in one of the vial, the means for establishing fluid communication between the pressurization gas conduit and the vial, and the pressurization gas conduit. It is still further contemplated that, when leaks are present within the head space sampling device, the escape of gas through the leaks can decrease the pressure within the pressurization gas conduit. In a further aspect, the step 200 of pressurizing the pressurization gas conduit can comprise pressurizing the pressurization gas conduit with the pressurization gas at a first flow rate to the first pressure. In this aspect, the first flow rate can range from about 5 to about 200 mL/min. referenced to 101.3 kPa and 25 degrees Celsius.

In another optional aspect, and with reference to FIG. 1, the step 200 of pressurizing the pressurization gas conduit can comprise pressurizing the pressurization gas conduit with the pressurization gas at a first flow rate to approach a predetermined pressure setpoint. It is contemplated that the pressurization gas conduit can be pressurized at the first flow rate to approach the predetermined pressure setpoint after fluid communication has been established between the head space and the pressurization gas conduit. In this aspect, the predetermined pressure setpoint can range from about 1 to about 100 pounds per square inch (psi) above ambient pressure, more preferably from about 5 to about 30 psi above ambient pressure. Alternatively, the first pressure can be referenced to a subambient pressure or to a pressure above ambient pressure. In a further aspect, the predetermined pressure setpoint can be an absolute pressure. In this aspect, the predetermined pressure setpoint can range from about 110 to about 800 kPa and more preferably from about 130 to about 310 kPa.

In an additional aspect, the first flow rate can range from about 5 to about 200 milliliters per minute (mL/min.) referenced to a pressure of 101.3 kPa and a temperature of 25 degrees Celsius. It is contemplated that, in the absence of leaks, the pressurization gas conduit can be pressurized to the predetermined pressure setpoint. Thus, following the establishment of fluid communication between the head space and the pressurization gas conduit, it is contemplated that a failure of the gas pressure within the pressurization gas conduit to achieve the predetermined pressure setpoint can be indicative of a leak, such as a leak in one of the vial, the means for establishing fluid communication between the pressurization gas conduit and the vial, and the pressurization gas conduit. It is further contemplated that, when leaks are present within the head space sampling device, the pressurization of the pressurization gas conduit at the first flow rate can be insufficient to compensate for the gas escaping through the leaks within the head space sampling device. Thus, when leaks are present within the head space sampling device, it can be necessary to actively adjust the flow rate of the pressurization gas to achieve or maintain the predetermined pressure setpoint.

Optionally, in an additional aspect, after the pressurization gas conduit is pressurized at the first flow rate, the method for detecting leaks can further comprise the step of allowing the gas pressure within the pressurization gas conduit to substantially stabilize. In this aspect, it is contemplated that, in the absence of leaks, after the gas pressure substantially stabilizes within the pressurization gas conduit, pressure within the pressurization gas conduit should be substantially static, and the flow of gas through the pressurization gas conduit should be substantially zero. Thus, after fluid communication has been established between the head space and the pressurization gas conduit, a non-zero flow rate following stabilization of the gas pressure can be indicative of a leak, such as a leak in one of the vial, the means for establishing fluid communication between the pressurization gas conduit and the vial, and the pressurization gas conduit. It is contemplated that, when leaks are present within the head space sampling device, the pressure within the pressurization gas conduit can be actively maintained by providing additional gas flow within the pressurization gas conduit and thereby compensating for the gas escaping through the leaks.

In some aspects, the head space sampling device can be in communication with a head space analyzer. In these aspects, the method for detecting leaks in the head space analysis device can comprise the step 240 of transferring the sample from the head space sampling device to the head space analyzer using conventional methods. In exemplary aspects, the head space analyzer can be connected with an analysis column for receiving at least a portion of the head space and can include a chromatographic detector in fluid communication with the analysis column and a chromatographic analyzer, such as those described herein.

In some aspects, when the head space sampling device comprises a sample loop, the sample loop of the head space sampling device can be connectable in fluid communication between either a ventilation pathway of the sampling device and the head space or between the sample loop and the head space analyzer. In one exemplary aspect, the ventilation pathway can comprise a ventilation valve. In this aspect, when the ventilation valve is connectable in fluid communication with the pressurization gas conduit, the sample loop of the head space sampling device can be connectable in fluid communication between either the pressurization gas conduit and the head space or between the sample loop and the head space analyzer. In this aspect, and with reference to FIG. 1, the step 240 of transferring the sample from the sample loop to the head space analyzer can comprise opening the ventilation valve of the head space sampling device such that at least a portion of the head space enters into the sample loop. In this aspect, the step 240 of transferring the sample can further comprise the step of disconnecting the sample loop of the head space sampling device from the pressurization gas. It is contemplated that the step 240 of transferring the sample can still further comprise connecting the sample loop to the head space analyzer. When the head space sampling device comprises a sample loop, it is contemplated that the head space analyzer can comprise a carrier gas conduit having an inlet for receiving a carrier gas. Thus, it is contemplated that the step 240 of transferring the sample can still further comprise pressurizing the carrier gas conduit with the carrier gas such that at least a portion of the head space within the sample loop is forced into the analysis column. In one exemplary aspect, it is contemplated that the sample loop can be attached to, or positioned within, a conventional valve for providing selective fluid communication between the sample loop and elements of the head space sampling device. For example, and without limitation, the sample loop can be attached to, or positioned within, a multi-port valve such as a six-port rotary valve, a multi-port diaphragm valve, and the like. It is further contemplated that the sample loop can be a part of a micromachined electromechanical system comprising a plurality of multi-port valves or diaphragm valves. It is still further contemplated that the sample loop can be a conventional chemical trap, such as those described herein.

Optionally, in one aspect, fluid communication between the head space and the pressurization gas conduit can be established prior to pressurization of the pressurization gas conduit. In this aspect, the method for detecting leaks can further comprise the step of measuring the pressure within the pressurization gas conduit prior to the pressurization of the pressurization gas conduit. It is contemplated that this pre-pressurization measurement of pressure within the pressurization gas conduit can be indicative of a poorly crimped or poorly secured vial. It is further contemplated that the head space sampling device can comprise means for providing an output indicative of the pre-pressurization pressure within the pressurization gas conduit, such as a controller as described herein. Optionally, in another aspect, the method for detecting leaks in the head space sampling device can further comprise measuring the change in pressure within the pressurization gas conduit before and after transfer of the sample to the head space analyzer. It is contemplated that this change in pressure within the pressurization gas conduit can be used to determine whether there were any abnormalities within the head space sampling device.

In an additional aspect, the head space sampling device can comprise a flow sensor for measuring the flow rate of the pressurization gas through the pressurization gas conduit. Optionally, the method for detecting leaks in the head space sampling device can further comprise the step of resetting the output of the flow sensor within the head space sampling device prior to pressurization of the pressurization gas conduit. In this aspect, it is contemplated that the head space sampling device can have a controller configured to "re-zero" the output of the flow sensor when substantially zero gas flow is present within the pressurization gas conduit, thereby accounting for any drifting of the flow signal measurements that may occur due to time or temperature. It is further contemplated that by ensuring that the flow sensor is re-zeroed prior to pressurization of the pressurization gas conduit, the flow sensors can more accurately measure smaller gas flow rates and can, therefore, more accurately detect leaks within the vial and the head space sampling device. In one aspect, the step of resetting the output of the flow sensor can occur after the valves within the head space sampling device have been closed such that the gas flow through the pressurization gas conduit is substantially zero. Thus, it is contemplated that the flow sensor can be zeroed out prior to the time when flow measurement within the head space sampling device is to occur.

In other exemplary aspects, as shown in FIG. 2, the method for detecting leaks in the head space sampling device can comprise the step 300 of pressurizing the pressurization gas conduit with the pressurization gas, as described herein. In an additional aspect, the method for detecting leaks can comprise the step 310 of monitoring the gas pressure within the pressurization gas conduit, as described herein. In another aspect, the method for detecting leaks can comprise the step 320 of monitoring the flow rate of the pressurization gas through the pressurization gas conduit, as described herein.

In an additional aspect, the method for detecting leaks in the head space sampling device can comprise the step 330 of establishing fluid communication between the head space and the pressurization gas conduit, as described herein. Optionally, in another aspect, the method for detecting leaks can further comprise the step of adjusting the temperature of the vial to produce a vapor in the head space, as described herein.

In one optional aspect, the means for establishing fluid communication between the pressurization gas conduit and the vial can comprise a transport conduit, which can be disposed between the pressurization gas conduit and the vial. In this aspect, it is contemplated that the step 330 of establishing fluid communication between the head space and the pressurization gas conduit can comprise the step of establishing fluid communication between the head space, the transport conduit, and the pressurization gas conduit. In another aspect, the means for establishing fluid communication between the head space and the pressurization gas conduit can further comprise a needle having a bore in fluid communication with the transport conduit. In this aspect, it is contemplated that the step of establishing fluid communication between the head space, the transport conduit, and the pressurization gas conduit can comprise penetrating a septum of the vial with the needle. It is contemplated that, when the pressurization gas conduit comprises a valve for controlling flow of pressurization gas through the pressurization gas conduit, the gas pressure within the pressurization gas conduit can be monitored at any position that is both upstream of the junction between the pressurization gas conduit and the transport conduit and downstream of the valve of the pressurization gas conduit.

Following the step of establishing fluid communication between the head space, the transport conduit, and the pressurization gas conduit, the method for detecting leaks can further comprise the step 340 of allowing the gas pressure within the pressurization gas conduit to substantially stabilize. In this aspect, it is contemplated that the step 340 of allowing the gas pressure within the pressurization gas conduit to stabilize can correspond to a substantially static pressure condition within the pressurization gas conduit, including a substantially constant pressure gradient.

In still a further aspect, the method for detecting leaks can further comprise the step 350 of comparing the monitored flow rate of the pressurization gas to an expected flow rate of the pressurization gas. As set forth herein, it is contemplated that the expected flow rate can correspond to the flow rate that should occur within the pressurization gas conduit in the absence of leaks within the head space sampling device and the vial. More particularly, it is contemplated that the expected flow rate of the pressurization gas corresponds to the monitored flow rate of the pressurization gas through the pressurization gas conduit prior to the step 330 of establishing fluid communication between the head space and the pressurization gas conduit. Thus, when the head space sampling device comprises a transport conduit, it is contemplated that a flow rate greater than the expected flow rate can be indicative of a leak, such as a leak in one of the vial, the transport conduit, and the pressurization gas conduit. It is further contemplated that, when leaks are present within the head space sampling device, the pressure within the pressurization gas conduit can be maintained by providing additional gas flow through the pressurization gas conduit and thereby compensating for the gas escaping through the leaks. In yet another aspect, for purposes of measuring the expected flow rate, when the head space sampling device comprises a transport conduit, the method for detecting leaks can further comprise the step of restricting gas flow between the pressurization gas conduit and the transport conduit.

In some aspects, the head space sampling device can be in communication with a head space analyzer. In these aspects, as shown in FIG. 2, the method for detecting leaks in the head space analysis device can comprise the step 360 of transferring the sample from the head space sampling device to the head space analyzer using conventional methods. In exemplary aspects, the head space analyzer can comprise an analysis column in fluid communication with the head space sampling device, a chromatographic detector in fluid communication with the analysis column, and a chromatographic analyzer, such as those described herein. In one aspect, when the head space sampling device comprises a transport conduit, the step 360 of transferring the sample from the head space sampling device to the head space analyzer can comprise the step of discontinuing pressurization of the pressurization gas conduit with the pressurization gas for a selected amount of time, thereby promoting flow of at least a portion of the head space to the head space analyzer.

It is contemplated that conventional processing techniques can be used to perform the steps of the methods disclosed herein. For example, it is contemplated that the disclosed method steps can be performed using conventional processing hardware, including, without limitation, a controller, a processor, a memory, a display, a user input mechanism such as a keyboard, and the like. It is further contemplated that the conventional processing hardware can be part of a conventional computer that can be used in conjunction with practicing the disclosed methods. In one aspect, the conventional processing hardware can be programmed by software to perform the steps of the disclosed methods.

Head space sampling devices that can be used to perform the steps of the previously described methods are also disclosed. Head space analysis systems comprising such head space sampling devices are also disclosed. In exemplary aspects, as shown in FIGS. 3-6, the head space sampling device 10, 110, 410, 510 can be configured to sample a gas sample from a head space 22 of a vial 20. It is contemplated that the vial 20 can be a conventional glass sample vial. It is further contemplated that the vial 20 can be configured to contain a head space having a volume ranging from about 6 milliliters (mL) to about 22 milliliters (mL). In this aspect, the head space sampling device 10, 110, 410, 510 can be configured to sample the gas sample from the head space 22 of the vial 20 using a pressurization gas. It is contemplated that the pressurization gas can be any gas that is substantially non-reactive or inert for purposes of a particular sample. Thus, it is contemplated that the pressurization gas can be, for example and without limitation, helium gas, hydrogen gas, nitrogen gas, argon gas, and the like. In one exemplary aspect, it is contemplated that the pressurization gas can be a mixture of methane and argon, such as, for example and without limitation, 5% methane in argon. In an additional aspect, it is contemplated that the vial 20 can comprise a septum 24. In this aspect, it is contemplated that the septum 24 can comprise a conventional elastomeric material, such as, for example and without limitation, rubber. It is further contemplated that the septum 24 can comprise Teflon®-coated silicone rubber.

In one aspect, and as shown in FIGS. 3-4, the head space sampling device 10, 110 can comprise a pressurization gas conduit 30, 130 in fluid communication with the vial 20. In this aspect, the pressurization gas conduit 30, 130 can have an inlet 31, 131 for receiving the pressurization gas and a valve 32, 132 for controlling flow of gas therethrough the pressurization gas conduit. It is contemplated that the valve 32, 132 can be a conventional electromechanical solenoid valve.

In an additional aspect, with reference to FIGS. 3-4, the head space sampling device 10, 110 can comprise a flow sensor 34, 134 for measuring gas flow through the pressurization gas conduit 30, 130. In this aspect, the flow sensor 34, 134 can be configured to generate a flow signal indicative of the gas flow through the pressurization gas conduit 30, 130. It is contemplated that the flow sensor 34, 134 can be a conventional thermal mass flow sensor. In another aspect, the head space sampling device 10, 110 can comprise a pressure sensor 36, 136 for measuring gas pressure within the pressurization gas conduit 30, 130. In this aspect, the pressure sensor 36, 136 can be configured to generate a pressure signal indicative of the gas pressure within the pressurization gas conduit 30, 130. It is contemplated that the pressure sensor 36, 136 can be a conventional piezoresistive pressure sensor.

In an additional aspect, and with reference to FIGS. 3-4, it is contemplated that the head space sampling device 10, 110 can comprise means for establishing fluid communication between the pressurization gas conduit 30, 130 and the vial 20 containing the head space 22. In one aspect, the means for establishing fluid communication between the pressurization gas conduit 30, 130 and the head space 22 can comprise a needle 26 having a bore in fluid communication with the pressurization gas conduit. In this aspect, it is contemplated that the septum 24 can be configured to form a seal around the needle 26 upon insertion of the needle into the head space 22 of the vial 20. It is contemplated that any conventional means for establishing fluid communication can be used to establish fluid communication between the pressurization gas conduit 30 and the head space 22. For example and without limitation, the means for establishing fluid communication between the pressurization gas conduit 30 and the vial 20 containing the head space 22 can comprise a stream selection valve for selective sampling through multiple vessels, as well as resealable valves for attachment to the vial, In a further aspect, the head space sampling device 10 can comprise a ventilation pathway. It is contemplated that the ventilation pathway can be positioned anywhere within the head space sampling device 10 provided the ventilation pathway is connectable to establish fluid communication between the head space 22 and the environment surrounding the head space sampling device 10, which can be, for example and without limitation, the ambient environment, a subambient environment, and an environment with pressures above ambient pressure. In one exemplary aspect, as depicted in FIG. 3, the ventilation pathway of the head space sampling device 10 can comprise a ventilation valve 38 in fluid communication with the pressurization gas conduit 30. In this aspect, it is contemplated that the ventilation valve 38 can be opened and closed to provide selective fluid communication between the pressurization gas conduit 30 and the environment surrounding the head space sampling device 10.

As shown in FIG. 3, in one exemplary aspect, when the ventilation pathway of the head space sampling device 10 comprises a ventilation valve 38 in fluid communication with the pressurization gas conduit 30, it is contemplated that the means for establishing fluid communication between the pressurization gas conduit and the vial 20 containing the head space 22 can comprise a sample loop 40. In this aspect, the sample loop 40 is connectable in fluid communication with the pressurization gas conduit 30 and the head space 22. In one exemplary aspect, it is contemplated that the sample loop can be attached to, or positioned within, a conventional valve for providing selective fluid communication between the sample loop and elements of the head space sampling device. For example, and without limitation, the sample loop can be attached to, or positioned within, a multi-port valve such as a six-port rotary valve, a multi-port diaphragm valve, and the like. It is further contemplated that the sample loop can be a part of a micro-machined electromechanical system comprising a plurality of multi-port valves or diaphragm valves. It is still further contemplated that the sample loop can be a conventional chemical trap, such as those described herein. In some embodiments, when the pressurization gas conduit 30 and the head space 22 are connected in fluid communication through the sample loop 40, all other ports or valves of the sample loop are closed, and the fluid in the pathways depicted in FIG. 3 is in a "closed system." The only outlet in this closed system is the ventilation valve 38.

As referenced above, for purposes of the head space sampling device 10 depicted in FIG. 3, the ventilation valve 38, which is connectable in fluid communication with pressurization gas conduit 30, serves as a ventilation pathway for the escape of portions of the head space through the sample loop. However, it is contemplated that the ventilation pathway, the sample loop 40, and the pressurization gas conduit 30 can be connected in any configuration for purposes of the disclosed methods, systems, and devices, provided (1) the pressurization gas conduit is connectable in fluid communication with the head space 22 of the vial 20 and (2) the sample loop is connectable between and in fluid communication with the head space of the vial and the ventilation pathway. Thus, in one aspect, it is contemplated that the ventilation pathway can be isolated and disconnected from the pressurization gas conduit 30.

Optionally, in one aspect, although not depicted in FIG. 3, the head space sampling device 10 can comprise a conventional chemical trap. In this aspect, it is contemplated that the chemical trap can be positioned within the pressurization gas conduit 30 between the ventilation valve 38 and the sample loop 40. It is further contemplated that the chemical trap can prevent portions of the sample from escaping to the atmosphere through the ventilation valve 38 and/or damaging the ventilation valve.

In another optional aspect, although not depicted in FIGS. 3 and 4, the head space sampling device 10, 110 can comprise means for adjusting the temperature of the sample within the vial 20. It is contemplated that the means for adjusting the temperature of the sample can comprise any conventional mechanism for controlling temperature, including, for example and without limitation, a hot plate, a traditional oven, a convection oven, a burner, a water bath, an oil bath, a cartridge heater, a heating mantle, a Peltier device, and the like.

In still another aspect, and with reference to FIGS. 3 and 4, the head space sampling device 10, 110 can comprise a controller 50, 150. In this aspect, the controller 50, 150 can be adapted to receive the flow signal from the flow sensor 34, 134 and the pressure signal from the pressure sensor 36, 136. As depicted in FIGS. 3 and 4, the controller 50, 150 can receive the flow signal from the flow sensor 34, 134 through electrical communication link 53, 153. As further depicted in FIGS. 3 and 4, the controller 50, 150 can receive the pressure signal from the pressure sensor 36, 136 through electrical communication link 54, 154. In an additional aspect, it is contemplated that the controller 50, 150 can control, and be in communication with, the valve 32, 132 of the pressurization gas conduit 30, 130. In this aspect, the controller 50, 150 can be configured to open and close the valve 32, 132 to control at least one of the pressure within and the flow through the pressurization gas conduit 30, 130. As depicted in FIGS. 3-4, the controller 50, 150 can communicate with the valve 32, 132 of the pressurization gas conduit 30, 130 through electrical communication link 52, 152. It is contemplated that electrical communication links 52, 53, 54, 152, 153, and 154 can comprise any conventional means for electrical communication, including, for example and without limitation, conventional wires and conventional wireless transmission mechanisms, including, for example and without limitation, radio frequency (RF) communication mechanisms and infrared (IR) communication mechanisms.

In one aspect, when the controller 50, 150 of the head space sampling device 10, 110 is adapted to receive the pressure signal from the pressure sensor 36, 136, the controller can be adapted to compare the pressure signal from the pressure sensor to a predetermined pressure setpoint. In this aspect, the controller 50, 150 can be further adapted to control the valve 32, 132 of the pressurization gas conduit 30, 130 by opening and closing the valve such that the pressure within the pressurization gas conduit approaches the predetermined pressure setpoint. It is contemplated that the predetermined pressure setpoint can range from about 1 to about 100 pounds per square inch (psi) above ambient pressure, and more preferably from about 5 to about 30 psi above ambient pressure. In another aspect, the predetermined pressure setpoint can be an absolute pressure. In this aspect, the predetermined pressure setpoint can range from about 110 to about 800 kPa, and more preferably from about 130 to about 310 kPa.

In another aspect, when the controller 50, 150 of the head space sampling device 10, 110 is adapted to receive the flow signal from the flow sensor 34, 134, the controller can be adapted to compare the flow signal from the flow sensor to a predetermined flow setpoint. In this aspect, the controller 50, 150 can be further adapted to control the valve 32, 132 of the pressurization gas conduit 30, 130 by opening and closing the valve such that the flow rate within the pressurization gas conduit approaches the predetermined flow setpoint. It is contemplated that the predetermined flow setpoint can range from about 5 to about 200 mL/min. referenced to 101.3 kPa and 25 degrees Celsius.

In still another aspect, the controller 50, 150 can be adapted to control the valve 32, 132 of the pressurization gas conduit 30, 130 by opening and closing the valve to selectively control either of the flow through the pressurization gas conduit or the pressure within the pressurization gas conduit. Thus, in this aspect, the controller 50, 150 can be adapted to dynamically shift from controlling the flow through the pressurization gas conduit 30, 130 to controlling the pressure within the pressurization gas conduit. For example, for a selected time period or under desired conditions, the controller 50, 150 can be adapted to control the valve 32, 132 of the pressurization gas conduit 30, 130 by opening and closing the valve such that the flow through the pressurization gas conduit approaches the predetermined flow setpoint, as described herein. At an appropriate time, the controller 50, 150 can be adapted to shift to controlling the valve 32, 132 of the pressurization gas conduit 30, 130 such that the pressure within the pressurization gas conduit approaches the predetermined pressure setpoint, as described herein.

In an additional aspect, the controller 50, 150 of the head space sampling device 10, 110 can be adapted to provide an output indicative of at least one of gas flow through the pressurization gas conduit 30, 130, gas pressure within the pressurization gas conduit, change in gas flow through the pressurization gas conduit, and change in gas pressure within the pressurization gas conduit. In this aspect, it is contemplated that the controller 50, 150 can be adapted to produce an alert to symbolize the presence of a leak within the head space sampling device 10, 110 according to user-defined criteria, such as, for example and without limitation, the measured flow rate and pressure within the pressurization gas conduit 30, 130. In another aspect, it is contemplated that the controller 50, 150 can be a single device or a plurality of devices connected in electrical communication with one another.

In a further aspect, the controller 50, 150 of the head space sampling device 10, 110 can be in electrical communication with the means for adjusting the temperature of the sample within the vial 20. In this aspect, it is contemplated that the controller 50, 150 can be selectively programmed by a user to adjust the temperature of the sample in a desired manner.

Optionally, in a further aspect, although not shown in FIG. 3, the controller 50 can control, and be in communication with, the ventilation valve 38. In this aspect, the controller 50 can be configured to open and close the ventilation valve 38 to control communication between the pressurization gas conduit 30 and the surrounding pressure environment.

In another aspect, the controller 50 can be configured to reset the output of each flow sensor within the head space sampling device 10 prior to pressurization of the vial 20. In this aspect, it is contemplated that the controller 50 can be configured to "re-zero" the output of each flow sensor when substantially zero gas flow is present within the pressurization gas conduit 30, thereby accounting for any drifting of the flow signal measurements that may occur due to time or temperature. It is further contemplated that by ensuring that each flow sensor is re-zeroed prior to pressurization of the vial 20, the flow sensors can more accurately measure smaller gas flow rates and can, therefore, more accurately detect leaks within the vial and the head space sampling device 10.

As shown in FIGS. 3-4, in another aspect, the head space sampling device 10, 110 can comprise a user interface 80, 180, such as, for example and without limitation, a computer having a keyboard and a monitor. In this aspect, the user interface 80, 180 of the head space sampling device 10, 110 can be in electrical communication with the controller 50, 150. In one aspect, the user interface 80, 180 can be configured to display the output of the controller 50, 150. In another aspect, the user interface 80, 180 can be configured to receive at least one input from a user of the head space sampling device 10, 110. In this aspect, it is contemplated that the at least one input from the user can comprise instructions for operation of the head space sampling device 10, 110 that are responsive to the output of the controller 50, 150. It is further contemplated that the at least one input from the user can comprise instructions for operation of the head space sampling device 10, 110, including, for example and without limitation, selected gas pressures and flow rates to be achieved and/or maintained within the pressurization gas conduit 30, 130, such as the predetermined pressure setpoints and predetermined flow setpoints disclosed herein. In some aspects, the controller 50, 150 and/or the user interface 80, 180 can comprise means for converting the at least one input from the user into a desired format. In exemplary aspects, it is contemplated that when the user interface 80, 180 receives an input from a user corresponding to a pressure or flow rate within the pressurization gas conduit, the user interface and/or the controller 50, 150 can be configured to convert the input into a desired format for controlling the operation of the head space sampling device 10, 110. For example, and without limitation, when the user interface 80, 180 receives an input from a user corresponding to a predetermined pressure setpoint in gauge pressure units or pressure units referenced to 1 atmosphere, such as pounds per square inch (psi), kPa, or bars, it is contemplated that the user interface and/or the controller 50, 150 can convert the input into a pressure value having a desired format, such as an absolute pressure value or a value calculated using a selected calibration factor.

In one exemplary aspect, and with reference to FIGS. 3-4, at least one of the user interface 80, 180 and the controller 50, 150 of the head space sampling device 10, 110 can have a memory for storing data files corresponding to respective samples. In this aspect, when the output of the controller 50, 150 of the head space sampling device 10, 110 is indicative of a leak in the head space sampling device, it is contemplated that the controller 50, 150 can be configured to store a leak entry in the memory of at least one of the user interface 80, 180 and the controller. When the output of the controller 50, 150 is indicative of a leak, it is further contemplated that the controller 50, 150 can be configured to flag the corresponding data file in the memory of at least one of the user interface 80, 180 and the controller. It is still further contemplated that, when the output of the controller 50, 150 is indicative of a leak, the user of the head space sampling device 10, 110 can enter an input into the user interface 80, 180 to indicate whether sampling and/or analysis of particular samples should continue. For example, when the head space sampling device 10, 110 is configured to sample the head spaces of a sequence of different vials, the user can enter an input into the user interface 80, 180 to indicate whether or not the head space sampling device should continue with sequential sampling and/or analysis of the head spaces 22 of the vials 20.

As shown in FIG. 4, in one optional aspect, the head space sampling device 110 can comprise a transport conduit 160 for providing fluid communication between the pressurization gas conduit 130 and the vial 20. In an additional aspect, and with reference to FIG. 4, it is contemplated that the head space sampling device 110 can comprise means for establishing fluid communication between the transport conduit 160 and the vial 20 containing the head space 22. In one aspect, the means for establishing fluid communication between the transport conduit 160 and the head space 22 can comprise a needle 26 having a bore in fluid communication with the transport conduit. In this aspect, it is contemplated that the septum 24 can be configured to form a seal around the needle 26 upon insertion of the needle into the head space 22 of the vial 20. It is contemplated that any conventional means for establishing fluid communication can be used to establish fluid communication between the transport conduit 160 and the head space 22. For example and without limitation, the means for establishing fluid communication between the transport conduit 160 and the vial 20 containing the head space 22 can comprise a stream selection valve for selective sampling through multiple vessels, as well as resealable valves for attachment to the vial.

In another aspect, and with reference to FIG. 4, the controller 150 can be adapted to compare the flow signal from the flow sensor 134 to an expected flow rate of the pressurization gas. It is contemplated that the controller 150 can compare the flow signal to the expected flow rate after the pressure within the pressurization gas conduit 130 is substantially stabilized. It is further contemplated that the controller 150 can compare the flow signal to the expected flow rate when a predetermined pressure setpoint is achieved within the pressurization gas conduit 130, as described herein. In one aspect, the expected flow rate of the pressurization gas can range from about 1 to about 15 mL per minute (mL/min.). It is contemplated that the expected flow rate can correspond to the flow rate that should occur within the pressurization gas conduit 130 in the absence of leaks. More particularly, in one exemplary aspect, the expected flow rate of the pressurization gas can correspond to the monitored flow rate of the pressurization gas prior to establishing fluid communication between the head space 22, the transport conduit 160, and the pressurization gas conduit 130. In an additional aspect, the head space sampling device 110 can comprise means for restricting flow of gas from the pressurization gas conduit 130 to the transport conduit 160. In this aspect, it is contemplated that, during measurement of the expected flow rate, the gas flow between the pressurization gas conduit 130 and the transport conduit 160 can be restricted.

In some aspects, the controller 50, 150 can comprise a processor. In this aspect, the processor can be programmed to operate in accordance with at least one of software, firmware, and field-programmable gate array (FPGA) code. It is contemplated that the controller 50, 150 can comprise a memory that is configured to store the software, firmware, and FPGA code that control the operation of the processor. Alternatively, the controller 50, 150 can be in communication with an external computer that stores the software, firmware and FPGA code. In one aspect, at least one of the software, firmware, and FPGA code can instruct the controller 50, 150 to detect leaks as disclosed herein. In an additional aspect, the controller 50, 150 can be configured to log the detection of a leak in the memory. In this aspect, it is contemplated that the log of detected leaks can enable a user of the system to identify results that should not be included in the analysis of the sample. In another aspect, at least one of the software, firmware, and FPGA code can instruct the controller 50, 150 to respond in a predetermined manner to detection of a leak. In this aspect, it is contemplated that the predetermined manner of responding to detection of a leak can comprise at least one of: prompting a user for instructions; aborting the analysis of the sample and advancing to the next sample; proceeding with analysis of the sample; aborting all analysis of the sample; activating an alarm; sending an alert e-mail to desired recipients; opening at least one valve within the head space sampling device 10; and closing at least one valve within the head space sampling device 10. In a further aspect, it is contemplated that the controller 50, 150 can be in communication with a keyboard. In this aspect, a user can use the keyboard to enter information for processing by the controller 50, 150. In still a further aspect, the controller 50, 150 can be in communication with a conventional display. In this aspect, the controller 50, 150 can be configured to display the outputs disclosed herein.

As set forth above, it is contemplated that the head space sampling device 10, 110 can be configured to detect leaks within not only the device itself, but also within the vial 20, at the connection between the head space sampling device and the vial, in the sample loop 40, and in the valves within the head space sampling device, such as a ventilation valve 38. Thus, it is contemplated that the head space sampling device 10, 110 can be configured to detect when an external leak is occurring at a fitting for the needle 26 that pierces the septum 24 of the vial 20 containing the sample. Similarly, it is contemplated that the head space sampling device 10, 110 can be configured to detect when the vial 20 has a poorly crimped cap or when the sample is otherwise exposed to the surrounding pressure environment. In some embodiments, the pressurization gas conduit 130 is connectable to a head space analyzer (indicated by a ∫ in FIG. 4). Thus, the fluid pathways shown in FIG. 4 can be an "open system," because the fluid in the head space sampling device can flow into the head space analyzer during leak testing as described in the present disclosure. As a result, leaks in the head space analyzer can be detected as well. It is contemplated that fluid communication can optionally be blocked between the head space analyzer and the head space sampling device when leaks within the sampling device are being tested. Then, fluid communication can be opened between the sampling device and the head space analyzer, and additional leaks can be detected.

In other aspects, and as depicted in FIGS. 5A-6, head space analysis systems for analyzing a gas sample from a head space 22 of a vial 20 are also disclosed. In these aspects, the head space analysis systems can be configured to analyze the gas samples using a pressurization gas.

In one aspect, as shown in FIGS. 5A-5B, the head space analysis system 400 can comprise a head space sampling device 410 and a head space analyzer 420. In this aspect, it is contemplated that the head space sampling device 410 of the head space analysis system 400 can comprise a pressurization gas conduit 430 having an inlet 431 and a valve 432, a flow sensor 434, a pressure sensor 436, a ventilation valve 438, means for establishing fluid communication between the pressurization gas conduit 430 and the vial 20 containing the head space 22, a controller 450, and electrical communication links 452, 453, 454, as described herein with reference to head space sampling device 10. In one aspect, the means for establishing fluid communication between the pressurization gas conduit 430 and the vial 20 can comprise a sample loop 440, as described herein with reference to head space sampling device 10. As depicted in FIG. 5A, when the pressurization gas conduit is connected to the sample loop 440, pressurization gas flows through the pressurization gas conduit 430, through the sample loop 440, and into the vial 20. In a further aspect, the means for establishing fluid communication between the pressurization gas conduit 430 and the vial 20 can comprise a needle 26 having a bore in fluid communication with the pressurization gas conduit, as described with reference to head space sampling device 10.

As shown in FIGS. 5A-5B, in one aspect, the head space analysis system can comprise a carrier gas conduit 422. In this aspect, the carrier gas conduit 422 can have an inlet 423 for receiving a carrier gas.

In some aspects, the head space analyzer 420 can be configured to analyze a sample from the head space 22 of the vial 20. More specifically, the head space analyzer 420 can be configured to receive a head space sample from the head space sampling device 410, send the head space sample into an analysis apparatus for analysis, and detect and report the result of the analysis. The analysis apparatus can be a user-selectable component that is not supplied with the head space analyzer 420, for example, a gas chromatography column. Typically, a user chooses a column and fits it into the head space analyzer 420 before operation of the head space analysis system 400. After the sample is analyzed by the gas chromatography column, the components of the sample pass through a detector in the head space analyzer 420 for detection. In some embodiments, the head space analyzer 420 may comprise a mass spectrometer. The sample can be directly analyzed and detected by a mass spectrometer without a separation step prior to mass spectrometry. Alternatively, the sample can be analyzed by a chromatography column first, followed by further analysis and detection by a mass spectrometer.

In another exemplary aspect, as shown in FIGS. 5A-5B, the analysis apparatus can comprise an analysis column 424, such as, for example and without limitation, a chromatography column. In a further aspect, the detector of the head space analyzer 420 can comprise a chromatographic detector 426. In this aspect, the chromatographic detector 426 can be in fluid communication with the analysis column 424. It is contemplated that the chromatographic detector can be configured to produce an output signal indicative of the components of the head space 22 within the vial 20. In still a further aspect, the head space analyzer 420 can comprise a chromatographic analyzer 428 adapted to receive and process the output signal from the chromatographic detector 426. As depicted in FIGS. 5A-5B, the chromatographic detector 426 can communicate with the chromatographic analyzer 428 through electrical communication link 427. In yet another aspect, the head space analyzer 420 can comprise a controller 460 as described herein. In this aspect, the controller 460 can control, and communicate with, the components of the head space analyzer, such as the chromatographic analyzer 428, through an electrical communication link 462. It is contemplated that electrical communication links 427 and 462 can comprise any conventional means for electrical communication, including, for example and without limitation, conventional wires and conventional wireless transmission mechanisms, including, for example and without limitation, radio frequency (RF) communication mechanisms and infrared (IR) communication mechanisms. Although not shown in FIGS. 5A-5B, it is contemplated that controllers 450 and 460 can be in communication with one or more user interfaces as described herein.

In these aspects, it is contemplated that the head space sampling device 410 can comprise a ventilation pathway. It is further contemplated that the sample loop 440 of the head space sampling device 410 is connectable to allow fluid communication either between the ventilation pathway and the head space 22 or between the sample loop 440 and the head space analyzer 420. For purposes of FIGS. 5A-5B, the ventilation valve 438, which is connectable in fluid communication with pressurization gas conduit 430, serves as a ventilation pathway for the escape of portions of the head space through the sample loop 440. However, it is contemplated that the ventilation pathway, the sample loop 440, and the pressurization gas conduit 430 can be connected in any configuration for purposes of the disclosed methods, systems, and devices, provided (1) the pressurization gas conduit is connectable in fluid communication with the head space 22 of the vial 20 and (2) the sample loop is connectable between and in fluid communication with the head space of the vial and the ventilation pathway. Thus, in one aspect, it is contemplated that the ventilation pathway can be isolated and disconnected from the pressurization gas conduit 430. In other aspects, when the sample loop 440 is connectable in fluid communication between the head space 22 and both the ventilation valve 438 and pressurization gas conduit 430, as shown in FIGS. 5A-5B, the sample loop 440 is connectable to allow fluid communication either between the pressurization gas conduit 430 and the head space 22 or between the sample loop and the head space analyzer 420. It is further contemplated that the sample loop is connectable to allow fluid communication between the sample loop and the carrier gas conduit 422. It is still further contemplated that when the sample loop 440 is in fluid communication with the head space analyzer 420, the carrier gas conduit 422 can be in fluid communication with the head space analyzer through the sample loop. Thus, as shown in FIGS. 5A-5B, in one exemplary aspect, the sample loop 440 is connectable to allow fluid communication either between the pressurization gas conduit 430 and the head space 22 or between the carrier gas conduit 422 and the analysis column 424. In one aspect, it is contemplated that the sample loop of the head space sampling device 410 is connectable in fluid communication with the surrounding pressure environment through the ventilation pathway. In this aspect, it is further contemplated that the surrounding pressure environment can be an ambient pressure environment, a subambient pressure environment, or an environment with a pressure above ambient pressure. As depicted in FIG. 5B, when the carrier gas conduit 422 is connected to the sample loop 440, carrier gas flows through the carrier gas conduit, through the sample loop, and into the analysis column 424. As depicted in FIG. 5A, when the pressurization gas conduit 430 is connected to the sample loop 440, the carrier gas conduit is not in fluid communication with the sample loop.

It is contemplated that the carrier gas, like the pressurization gas, can be any gas that is substantially non-reactive or inert for purposes of a particular sample. Thus, it is contemplated that the carrier gas can be, for example and without limitation, helium gas, hydrogen gas, nitrogen gas, argon gas, and the like. In one exemplary aspect, it is contemplated that the carrier gas can be a mixture of methane and argon, such as, for example and without limitation, 5% methane in argon. Therefore, it is further contemplated that the carrier gas can have the same chemical characteristics as the pressurization gas, as described herein. However, it is also contemplated that the carrier gas can have different chemical characteristics than the pressurization gas. In one aspect, it is still further contemplated that the pressurization gas and the carrier gas can serve different purposes within head space analysis system 400. For example, for purposes of head space analysis system 400, the pressurization gas can be used to pressurize the pressurization gas conduit 430 and the vial 20 containing the head space, whereas the carrier gas can be used to transport at least a portion of the gas sample within the sample loop 440 to the head space analyzer 420.

In an additional aspect, it is contemplated that the head space analyzer 420 of the head space analysis system 400 can comprise any analytical device that can make measurements of gaseous samples, including, for example and without limitation, a gas chromatograph, a mass spectrometer, a gas phase infrared spectrometer, a sensor array, and the like. In another aspect, it is contemplated that the head space analyzer 420 can be configured to trap the head space components of the vial 20 in a chemical trap, such as, for example and without limitation, activated charcoal, Tenax®, cold finger, and the like. In this aspect, the trapped head space components can be desorbed thermally into the gas phase or by a liquid using conventional methods. It is further contemplated that, when the head space components are desorbed in a liquid as described, the head space analyzer 420 can comprise any analytical device that can make measurements of liquid samples, including, for example and without limitation, a high performance liquid chromatograph, a liquid spectrometer, and the like.

Optionally, in another aspect, and as shown in FIGS. 5A-5B, the head space analysis system 400 can comprise a system controller 470. In this aspect, it is contemplated that the system controller 470 can be in communication with at least one of the controller 450 of the head space sampling device 410 and the controller 460 of the head space analyzer 420 to thereby provide overall control over the head space analysis system 400. It is contemplated that the system controller 470 can be in communication with the controller 450 of the head space sampling device 410 through electrical communication link 472. It is further contemplated that the system controller 470 can be in communication with the controller 460 of the head space analyzer 420 through electrical communication link 474. It is still further contemplated that the system controller 470 can be any conventional electrical communication system that is configured to communicate with the head space sampling device 410 and the head space analyzer 420, such as a controller as described herein. In one aspect, controller 450 of the head space sampling device 410 can be in communication with the controller 460 of the head space analyzer 420 through electrical communication link 455. It is contemplated that electrical communication links 455, 472, and 474 can comprise any conventional means for electrical communication, including, for example and without limitation, conventional wires and conventional wireless transmission mechanisms, including, for example and without limitation, radio frequency (RF) communication mechanisms and infrared (IR) communication mechanisms.

In an additional aspect, the system controller 470 can be in communication with a user interface 480, as described herein, through electrical communication link 476. It is contemplated that electrical communication link 476 can comprise any conventional means for electrical communication, including, for example and without limitation, conventional wires and conventional wireless transmission mechanisms, including, for example and without limitation, radio frequency (RF) communication mechanisms and infrared (IR) communication mechanisms. It is further contemplated that the user interface 480 can be configured to display an output of the system controller 470. In another aspect, it is contemplated that the user interface 480 can be configured to receive at least one input from a user of the head space analysis system 400. In this aspect, it is contemplated that the at least one input from the user can comprise instructions for operation of the head space sampling device 410, such as instructions that are responsive to the output of the system controller 470. It is further contemplated that the at least one input from the user can comprise instructions for operation of the head space analyzer 420, such as instructions that are responsive to the output of the system controller 470. In one exemplary aspect, the user interface 480 of the head space analysis system 400 can have a memory for storing data files corresponding to respective samples. In this aspect, the user interface 480 can be configured to associate outputs from the head space sampling device 410 and the head space analyzer 420 that result from the sampling and analysis of a particular sample.

In an alternative aspect, and as shown in FIG. 6, the head space analysis system 500 can comprise a head space sampling device 510 and a head space analyzer 520. In this aspect, it is contemplated that the head space sampling device 510 of the head space analysis system 500 can comprise a pressurization gas conduit 530 having an inlet 531 and a valve 532, a flow sensor 534, a pressure sensor 536, a transport conduit 560, means for establishing fluid communication between the transport conduit 560 and the vial 20 containing the head space 22, a controller 550, and electrical communication links 552, 553, 554, as described herein with reference to head space sampling device 110.

In some aspects, the head space analyzer 520 can be configured to analyze a sample from the head space 22 of the vial 20. More specifically, the head space analyzer 520 can be configured to receive a head space sample from the head space sampling device 510, send the fluid sample into an analysis apparatus for analysis, and detect and report the result of the analysis. The analysis apparatus can be a user-selectable component that is not supplied with the head space analyzer 520, for example, a gas chromatography column. Typically, a user chooses a column and fits it into the head space analyzer 520 before operation of the head space analysis system 500. After the sample is analyzed by the gas chromatography column, the components of the sample pass through a detector in the head space analyzer 520 for detection. In some embodiments, the head space analyzer 520 may comprise a mass spectrometer. The sample can be directly analyzed and detected by a mass spectrometer without a separation step prior to mass spectrometry. Alternatively, the sample can be analyzed by a chromatography column first, followed by further analysis and detection by a mass spectrometer.

In one exemplary aspect, as shown in FIG. 6, the analysis apparatus can comprise an analysis column 524, such as, for example and without limitation, a chromatography column. In this aspect, the analysis column 524 can be in fluid communication with the pressurization gas conduit 530. In a further aspect, the detector of the head space analyzer 520 can comprise a chromatographic detector 526. In this aspect, the chromatographic detector 526 can be in fluid communication with the analysis column 524. It is contemplated that the chromatographic detector 526 can be configured to produce an output signal indicative of the components of the head space 22 within the vial 20. In still a further aspect, the head space analyzer 520 can comprise a chromatographic analyzer 528 adapted to receive and process the output signal from the chromatographic detector 526. In this aspect, it is contemplated that the chromatographic analyzer 528 can communicate with the chromatographic detector 526 through electrical communication link 527. In yet another aspect, the head space analyzer 520 can comprise a controller 540 as described herein. In this aspect, the controller 540 can control, and communicate with, the components of the head space analyzer 520, such as the chromatographic analyzer 528, through an electrical communication link 542. It is contemplated that electrical communication links 527 and 542 can comprise any conventional means for electrical communication, including, for example and without limitation, conventional wires and conventional wireless transmission mechanisms, including, for example and without limitation, radio frequency (RF) communication mechanisms and infrared (IR) communication mechanisms. Although not shown in FIG. 6, it is contemplated that controllers 540 and 550 can be in communication with one or more user interfaces as described herein.

In an additional aspect, it is contemplated that the head space analyzer 520 of the head space analysis system 500 can comprise any analytical device that can make measurements of gaseous samples, including, for example and without limitation, a gas chromatograph, a mass spectrometer, a gas phase infrared spectrometer, a sensor array, and the like. In another aspect, it is contemplated that the head space analyzer 520 can be configured to trap the head space components of the vial 20 in a chemical trap, such as, for example and without limitation, activated charcoal, Tenax®, cold finger, and the like. In this aspect, the trapped head space components can be desorbed thermally into the gas phase or by a liquid using conventional methods. It is further contemplated that, when the head space is desorbed in a liquid as described, the head space analyzer 520 can comprise any analytical device that can make measurements of liquid samples, including, for example and without limitation, a high performance liquid chromatograph, a liquid spectrometer, and the like. In a further aspect, the means for establishing fluid communication between the transport conduit 560 and the vial 20 can comprise a needle 26 having a bore in fluid communication with the transport conduit, as described herein with reference to head space sampling device 110.

For purposes of head space analysis system 500, it is contemplated that the pressurization gas can serve the role of a conventional pressurization gas as well as the role of a conventional carrier gas. Therefore, for purposes of head space analysis system 500, the pressurization gas can be used to pressurize the pressurization gas conduit 530 as well as the vial 20 containing the head space 22. In addition, the pressurization gas can be used to transport at least a portion of head space 22 from the vial 20 to the head space analyzer 520.

Optionally, in another aspect, and as shown in FIG. 6, the head space analysis system 500 can comprise a system controller 570. In this aspect, it is contemplated that the system controller 570 can be in communication with at least one of the controller 550 of the head space sampling device 510 and the controller 540 of the head space analyzer 520 to thereby provide overall control over the head space analysis system 500. It is contemplated that the system controller 570 can be in communication with the controller 550 of the head space sampling device 510 through electrical communication link 572. It is further contemplated that the system controller 570 can be in communication with the controller 540 of the head space analyzer 520 through electrical communication link 574. It is still further contemplated that the system controller 570 can be any conventional electrical communication system that is configured to communicate with the head space sampling device 510 and the head space analyzer 520, such as a controller as described herein. In one aspect, controller 550 of the head space sampling device 510 can be in communication with the controller 540 of the head space analyzer 520 through electrical communication link 545. It is contemplated that electrical communication links 545, 572, and 574 can comprise any conventional means for electrical communication, including, for example and without limitation, conventional wires and conventional wireless transmission mechanisms, including, for example and without limitation, radio frequency (RF) communication mechanisms and infrared (IR) communication mechanisms.

In an additional aspect, as shown in FIG. 6, the system controller 570 can be in communication with a user interface 590, as described herein, through electrical communication link 576. It is contemplated that electrical communication link 576 can comprise any conventional means for electrical communication, including, for example and without limitation, conventional wires and conventional wireless transmission mechanisms, including, for example and without limitation, radio frequency (RF) communication mechanisms and infrared (IR) communication mechanisms. It is further contemplated that the user interface 590 can be configured to display an output of the system controller 570. In another aspect, it is contemplated that the user interface 590 can be configured to receive at least one input from a user of the head space analysis system 500. In this aspect, it is contemplated that the at least one input from the user can comprise instructions for operation of the head space sampling device 510, such as instructions that are responsive to the output of the system controller 570. It is further contemplated that the at least one input from the user can comprise instructions for operation of the head space analyzer 520, such as instructions that are responsive to the output of the system controller 570. In one exemplary aspect, the user interface 590 of the head space analysis system 500 can have a memory for storing data files corresponding to respective samples. In this aspect, the user interface 590 can be configured to associate outputs from the head space sampling device 510 and the head space analyzer 520 that result from the sampling and analysis of a particular sample.

Although several embodiments of the invention have been disclosed in the foregoing specification, it is understood by those skilled in the art that many modifications and other embodiments of the invention will come to mind to which the invention pertains, having the benefit of the teaching presented in the foregoing description and associated drawings. It is thus understood that the invention is not limited to the specific embodiments disclosed hereinabove, and that many modifications and other embodiments are intended to be included within the scope of the appended claims. Moreover, although specific terms are employed herein, as well as in the claims which follow, they are used only in a generic and descriptive sense, and not for the purposes of limiting the described invention, nor the claims which follow.

What is claimed is:

1. A head space sampling device for sampling a gas sample from a head space of a vial using a pressurization gas, said head space sampling device comprising:
   a pressurization gas conduit configured to be in fluid communication with said vial, said pressurization gas conduit comprising:
   an inlet for receiving said pressurization gas; and
   a valve for controlling flow of gas therethrough said pressurization gas conduit;
   a flow sensor for measuring gas flow through said pressurization gas conduit, said flow sensor generating a flow signal indicative of said gas flow;
   a pressure sensor for measuring gas pressure within said pressurization gas conduit, said pressure sensor generating a pressure signal indicative of said gas pressure; and
   a controller adapted to receive said flow signal from said flow sensor and said pressure signal from said pressure sensor, said controller being in communication with and controlling said valve of said pressurization gas conduit by opening and closing said valve to selectively control either of said flow through said pressurization gas conduit or said pressure within said pressurization gas conduit.

2. An analysis system comprising the head space sampling device according to claim 1, further comprising a head space analyzer, said head space analyzer configured to receive a head space sample from said head space sampling device and to send said head space sample to an analysis apparatus for analysis, said head space analyzer comprising a detector configured to produce an output signal indicative of the components within said head space sample.

3. An analysis system according to claim 2, further comprising a sample loop, said sample loop being connectable to allow fluid communication either between said pressurization gas conduit and said head space or between said sample loop and said head space analyzer.

4. A head space sampling device for sampling a gas sample from a head space of a vial using a pressurization gas, said head space sampling device comprising:
   a pressurization gas conduit configured to be in fluid communication with said vial, said pressurization gas conduit comprising:
   an inlet for receiving said pressurization gas; and
   a valve for controlling flow of gas therethrough said pressurization gas conduit;
   a flow sensor for measuring gas flow through said pressurization gas conduit, said flow sensor generating a flow signal indicative of said gas flow;
   a pressure sensor for measuring gas pressure within said pressurization gas conduit, said pressure sensor generating a pressure signal indicative of said gas pressure; and
   a controller adapted to receive said flow signal from said flow sensor and said pressure signal from said pressure sensor, said controller being in communication with and controlling said valve of said pressurization gas conduit by opening and closing said valve to selectively control either of said flow through said pressurization gas conduit or said pressure within said pressurization gas conduit, said controller being further adapted to: compare said pressure signal from said pressure sensor to a predetermined pressure setpoint; and to control said valve of said pressurization gas conduit by opening and closing said valve such that the pressure within said pressurization gas conduit approaches said predetermined pressure setpoint.

5. A head space sampling device for sampling a gas sample from a head space of a vial using a pressurization gas, said head space sampling device comprising:
   a pressurization gas conduit configured to be in fluid communication with said vial, said pressurization gas conduit comprising:
   an inlet for receiving said pressurization gas; and a valve for controlling flow of gas therethrough said pressurization gas conduit;

a flow sensor for measuring gas flow through said pressurization gas conduit, said flow sensor generating a flow signal indicative of said gas flow;

a pressure sensor for measuring gas pressure within said pressurization gas conduit, said pressure sensor generating a pressure signal indicative of said gas pressure; and a controller adapted to receive said flow signal from said flow sensor and said pressure signal from said pressure sensor, said controller being in communication with and controlling said valve of said pressurization gas conduit by opening and closing said valve to selectively control either of said flow through said pressurization gas conduit or said pressure within said pressurization gas conduit, said controller being further adapted to: compare said flow signal from said flow sensor to a predetermined flow setpoint; and to control said valve of said pressurization gas conduit by opening and closing said valve such that the flow rate within said pressurization gas conduit approaches said predetermined flow setpoint.

6. A head space sampling device for sampling a gas sample from a head space of a vial using a pressurization gas, said head space sampling device comprising:

a pressurization gas conduit configured to be in fluid communication with said vial, said pressurization gas conduit comprising:

an inlet for receiving said pressurization gas; and a valve for controlling flow of gas therethrough said pressurization gas conduit;

a flow sensor for measuring gas flow through said pressurization gas conduit, said flow sensor generating a flow signal indicative of said gas flow;

a pressure sensor for measuring gas pressure within said pressurization gas conduit, said pressure sensor generating a pressure signal indicative of said gas pressure;

a controller adapted to receive said flow signal from said flow sensor and said pressure signal from said pressure sensor, said controller being in communication with and controlling said valve of said pressurization gas conduit by opening and closing said valve to selectively control either of said flow through said pressurization gas conduit or said pressure within said pressurization gas conduit; and a transport conduit for providing fluid communication between said pressurization gas conduit and said vial, wherein, following stabilization of said gas pressure within said pressurization gas conduit, said controller is configured to compare said flow rate of said pressurization gas to an expected flow rate of said pressurization gas.

\* \* \* \* \*